United States Patent
Neudecker et al.

(10) Patent No.: US 6,756,045 B1
(45) Date of Patent: Jun. 29, 2004

(54) TOPICALLY APPLIED IDEBENONE-CONTAINING AGENT WITH PROTECTIVE AND REGENERATIVE EFFECT

(76) Inventors: Birgit Neudecker, Gottfried-Kellerstr 10, D-34233 Fuldatal-Rothwesten (DE); Eberhard Wieland, Stumpfe Elche 80, D-37077 Goettingen (DE); Falko Diedrich, Arn Hang 16, D-34260 Kaufungen (DE)

( * ) Notice: Subject to any disclaimer, the term of this patent is extended or adjusted under 35 U.S.C. 154(b) by 0 days.

(21) Appl. No.: 10/030,842

(22) PCT Filed: May 19, 2000

(86) PCT No.: PCT/DE00/01636

§ 371 (c)(1), (2), (4) Date: Jan. 9, 2002

(87) PCT Pub. No.: WO01/03657

PCT Pub. Date: Jan. 18, 2001

(30) Foreign Application Priority Data

Jul. 9, 1999 (DE) .......................... 199 32 197

(51) Int. Cl.$^7$ .......................... A61K 7/00; A61K 31/74; A61K 31/12; A61K 31/015; A01N 25/00

(52) U.S. Cl. .................. 424/401; 424/78.03; 514/675; 514/763; 514/845

(58) Field of Search .............................. 424/401, 78.03; 514/675, 763, 845

(56) References Cited

U.S. PATENT DOCUMENTS

| | | | | |
|---|---|---|---|---|
| 4,144,325 | A | | 3/1979 | Voyt .......................... 424/59 |
| 4,248,861 | A | | 2/1981 | Schutt .......................... 424/60 |
| 4,436,753 | A | | 3/1984 | Imada et al. .................. 424/331 |
| 5,059,627 | A | | 10/1991 | Goto et al. .................. 514/688 |
| 5,916,925 | A | | 6/1999 | Higuchi et al. ............. 514/678 |
| 5,958,883 | A | * | 9/1999 | Snow .......................... 514/16 |
| 6,437,003 | B1 | * | 8/2002 | Roullet et al. ............... 514/725 |
| 6,537,969 | B1 | * | 3/2003 | Blass .......................... 514/23 |

FOREIGN PATENT DOCUMENTS

| | | |
|---|---|---|
| DE | 3049039 | 3/1984 |
| EP | 0788793 | 8/1997 |
| JP | 01279818 | 11/1989 |
| JP | 4099719 | 3/1992 |
| JP | 4099719 | 8/1992 |
| JP | 11116470 | 4/1999 |
| WO | 9420068 | 9/1994 |
| WO | 9907355 | 2/1999 |

OTHER PUBLICATIONS

Machine Translation of JP 11–116470 (Apr. 27, 1999), Igari et al.*

Schaffler et al. "Dose–effect Relationship of Idebenone in an Experimental Cerebral Deficit Model" 1998, pp. 720–726, in Arzneim.–Forsch. / Drug. Res. Nr. 7 Abstract.

Schuetz et al. "Suppression of Leukocyte–Enhanced Cold Ischemia/Reperfusion Injury of Liver Endothelium with the Benzoquinone Antioxidant Idebenone" Dec., 1997, pp. 619–624, in Clinical Biochemistry, vol. 30.

Wieland et al. "Lipid hydroperoxide determination in serum by HPLC and iodometry" 1992, pp. 62–63, in Fresenius J. Anal Chem.

Michiels et al. "Cytotoxity of linoleic acid peroxide, malondialdahyde and 4–hydroxynonenal towards human fibroblasts" 1991, pp. 225–234, in Toxicology.

Deflandre et al. "Photostbility assessment of sunscreens. Benzylidene camphor and dibenzoylmethane derivatives" 1988, pp. 53–62, in International Journal of Cosmetic Science.

Yoshiki Miyachi "Skin diseases associated with oxidative injury" in Chapter 16 of "Oxidative Stress in Dermatology" 1993, pp. 323–331.

Thiele et al. "Depeltion of Human Stratum Corneum Vitamin E: An Early and Sensitive In Vivo Marker of Induced Photo–Oxidation" 1998, pp. 756–761, in The Journal of Investigative Dermatology.

Barkworth et al. "An Early Phase I Study to Determine th Tolerance, Safety and Pharmacokinetics of Idebone Following Multiple Oral Doses" 1985, pp. 1704–1707, in Arzneim.–Forsch./Drug Res. 1985.

Voelckel et al. "Vorkommen und Phot–Isomerisierung der Urocansaeure im stratum corneum bei polymorpher Lichtdermatose (PLD) Vergleichende Untersuchung bei PLD–Patienten und Hautgesunden" 1989, pp. 1–15, in Zentralblatt Haut– und Geschlechtskrankheiten (see application text for English description) Abstract.

* cited by examiner

Primary Examiner—Shengjun Wang
(74) Attorney, Agent, or Firm—Davidson Davidson & Kappel, LLC

(57) ABSTRACT

A regenerative or protective topical skin preparation includes idebenone (6-(10-hydroxydecyl)-2,3-dimethoxy-5-methyl-1,4-benzochinol) or a derivative of idebenone.

44 Claims, No Drawings

US 6,756,045 B1

TOPICALLY APPLIED IDEBENONE-CONTAINING AGENT WITH PROTECTIVE AND REGENERATIVE EFFECT

This application is a 371 of PCT/DE00/01636, filed May 19, 2000, which claims the priority of DE 19932197.03, filed Jul. 9, 1999.

BACKGROUND

The present invention relates to cosmetic and topical dermatological preparations containing an effective amount of idebenone and/or its derivatives. The present invention relates in particular to cosmetic preparations having effective protection from damaging oxidation processes in the skin, but also for the protection of cosmetic preparations themselves, or for the protection of the constituents of cosmetic preparations from damaging oxidation processes. Furthermore, the present invention relates to cosmetic and dermatological preparations containing an effective amount of idebenone and/or its derivatives, which beyond supporting vesicular breathing/cellular respiration or stabilisation of the mitochondrial membranes, promote the regeneration and vitality of skin cells.

The present invention also relates to anti-oxidants, and here preferably those which are used in skin-care cosmetic or dermatological preparations. The invention also relates particularly to cosmetic and dermatological preparations containing such anti-oxidants in combination with idebenone and/or its derivatives. Furthermore, the present invention relates to cosmetic and dermatological preparations for the prophylaxis and treatment of cosmetic and dermnatological skin changes, such as for example skin aging, and here in particular skin aging produced by oxidative or degenerative processes.

Furthermore, the present invention also relates to cosmetic and topical dermatological preparations, in which idebenone and its derivatives are used together with glycosaminoglycans and their salts, in particular hyaluronic acid having a molecular weight of 1 to 1,000,000 and their salts, or hyaluronidase inhibitors, such as for example inter-alpha-trypsin inhibitor. In addition, the present invention also relates to cosmetic and dermatological preparations, in which idebenone and/or its derivatives are esterified using glycosaminoglycans and/or their salts, in particular hyaluronic acid having a molecular weight of 1 to 1,000,000 and their salts or hyaluronidase inhibitors, such as for example inter-alpha-trypsin inhibitor.

Furthermore, the present invention relates to active ingredients and preparations containing those active ingredients for the prophylaxis of erythematous, inflammatory, allergic or autoimmune-reactive symptoms, in particular dermatoses.

The present invention also relates to active ingredient combinations and preparations which serve for the prophylaxis and treatment of light-sensitive skin, in particular photodermatoses.

The damaging effect of the ultraviolet part of solar radiation on the skin is generally known.

While rays having a wavelength which is less than 290 nm, (the so-called UVC range) are absorbed by the ozone layer in the earth's atmosphere, rays in the range between 290 nm and 320 nm, the so-called UVB range, cause an erythema, simple sunburn or even more or less severe burns.

The narrower range around 308 nm is given as a maximum for erythema activity of sunlight. For protection against UVB radiation, numerous compounds are known, in which they are derivatives of 3-benzylidene camphor, 4-aminobenzoic acid, cinnamic acid, salicylic acid, benzophenone and also 2-phenylbenzimidazole.

Also, for the range between about 320 nm and about 400 nm, the so-called UVA range, it is important to have filter substances available, since its rays may cause reactions in light-sensitive skin. It has been proved that UVA radiation leads to damage of the elastic and collagenic fibres of the connective tissue, which allows the skin to age prematurely, and that it is to be regarded as a cause of numerous phototoxic and photoallergic reactions. The damaging influence of UVB radiation may be amplified by UVA radiation. It has also been proved that consumption of lipophilic anti-oxidants, for example alpha-tocopherol, is triggered in the skin by UVA and UVB radiation (Thiele et al., J. Invest. Dermatol. 110, page 756 ff. (1998)).

For protection against the rays of the UVA range, certain derivatives of dibenzoylmethane have therefore been used, the photostability of which (Int. J. Cosm. Science 10, 53 (1988)) is not provided to an adequate extent. However, UV radiation may also lead to photochemical reactions, wherein then the photochemical reaction products intervene in the skin mechanism.

Predominantly such photochemical reaction products are free-radical compounds, for example hydroxy radicals. Also, undefined free-radial photoproducts, which are produced in the skin itself, may trigger uncontrolled side reactions due to their high reactivity. However, singlet oxygen, a non-free-radical excited state of the oxygen molecule, may occur on UV irradiation, likewise short-lived epoxides and many others. Singlet oxygen, for example is characterised with respect to the normally existing triplet oxygen (free-radical base state) by increased reactivity. Nevertheless, excited, reactive (free-radical) triplet states of the oxygen molecule also exist. Furthermore, there is the occurrence of lipid peroxidation products, such as for example hydroperoxides and aldehydes, wherein first in turn free-radical chain reactions may be triggered and to which overall cytotoxic properties have to be ascribed (Michiels and Remacle, Toxicology, 66, 225 ff. (1990)).

Furthermore, UV radiation is ionising radiation. Hence, there is the risk that also ionic species are produced on UV exposure, which then in turn are able to intervene oxidatively in the biochemical processes.

In order to prevent these reactions, additional anti-oxidants and/or free-radical absorbers/scavengers may be incorporated in the cosmetic or dermatological formulations.

It has already been proposed to use vitamin E, a substance having known anti-oxidative action in sunscreen formulations, nevertheless even here the action achieved remains far below that hoped for. The production of pro-oxidative degradation products of tocopherol should be mentioned.

Patent Documents DE 3 049 039, European 0 788 793 (13.8.1997), U.S. Pat. No. 4,436,753, U.S. Pat. No. 5,059,627, U.S. Pat. No. 5,916,925 and World 99 07 355 (see examples) indeed describe oral, parenteral or percutaneous preparations containing idebenone or its derivatives for the treatment of dementia, circulatory disturbances or for the induction of a neural growth factor. Patent document JP 1 279 818 describes the use of idebenone and its derivatives in various preparations for colouring hair. Idebenone showed no toxic effects on oral administration (Barkworth et al., Arzneim.-Forsch/Drug Res. 35 (II), 11, pages 1704 ff. (1985)).

Other investigations have also shown that idebenone and/or its derivatives shows protection against the loss of alpha-tocopherol and coenzyme Q-10 in the tissue under pro-oxidative conditions (Schütz et al., Clin. Biochem. 30, 619 ff. (1997)).

Light-sensitive skin includes photodermatoses. Further designations for the polymorphic light-dermatosis are PLD, PLE, Mallorca Acne and a plurality of further designations, as are given in the literature (for example A. Voelckel et al., Zentralblatt Hautund Geschlechtskrankheiten (1989), 156, page2).

Erythematous skin symptoms also occur as concomitant symptoms in ceratin skin diseases or skin irregularities. For example, the typical rash in the clinical picture of acne is regularly reddened to a greater or lesser extent.

Anti-oxidants are mainly used a protectie substances against the decay of the preparations containing them. Nevertheless, it is known that undesirable oxidation processes may also occur in the human and animal skin. Such processes play a considerabe part in skin aging.

Oxidative damage to the skin and its more detailed causes are listed in the essay "Skin Diseases Associated with Oxidative Injury" in "Oxidative Stress in Dermatology", page 323 ff. (Marcel Decker Inc., New York, Basle, Hong Kong, Publisher: Jürgen Fuchs, Frankfurt, and Lester Packer, Berkeley/Calif.).

Anti-oxidants are substances which prevent oxidation processes or which prevent the autooxidation of fats containing unsaturated compounds. Anti-oxidants which are also used in the field of cosmetics and pharmacy are, for example alpha-tocopherol, in particular in the form of alpha-tocopheryl acetate, sesamol, colic acid derivatives, butylhydroxy anisole and butylhydroxy toluene.

Anti-oxidants and/or free-radical absorbers may additionally be incorporated into cosmetic formulations also for the reason for preventing such reactions.

Indeed, some anti-oxidants and free-radical absorbers are known. Hence, it has already been proposed in United States patent specifications 4 144 325 and 4 248 861 and from numerous other documents, to use vitamin E, a substance having known antioxidative effect in sunscreen formulations, nevertheless here too the effect achieved remains far below that hoped for.

SUMMARY OF THE INVENTION

It is an object of the present invention to provide cosmetic and dermatological preparations and sunscreen formulations, which serve for the prophylaxis and treatment of light-sensitive skin, in particular photodermatoses, preferably PLD.

It is also an object of the present invention is to eliminate disadvantages of the state of the art. In particular, active ingredients or preparations containing such active ingredients should be provided, which when used may reduce the damage to the skin by oxidative influence, if not completely prevent it and which additionally show a regenerating and vitalising effect on aging, stressed or damaged skin by supporting vesicular breathing, stabilisation of mitochondrial membranes and anti-apoptotic properties.

In particular, active ingredients and preparations containing such active ingredients should be provided for cosmetic and dermatological treatment and/or prophylaxis of erythematous, inflanmmatory, allergic or autoimmune-reactive symptoms, in particular dermatoses, but also the clinical picture of "stinging".

The present invention provides a topical skin preparation including an amount of an agent effective for prophylaxis and/or treatment of a skin change and a topical carrier. The agent includes idebenone, a derivative of idebenone, or a combination of idebenone and the derivative of idebenone.

The present invention also provides a method for preventing and/or treating a skin change including applying a topical preparation to the skin. The preparation includes an effective amount of an agent effective for preventing and/or treating the skin change. The agent includes idebenone, a derivative of idebenone, or a combination of idebenone and the derivative of idebenone.

It was however surprising and not foreseeable for the expert that the use of idebenone and/or its derivatives as anti-oxidant and/or as free-radical absorber with the additional functions as stabiliser of mitochondrial membranes, stimulator of vesicular breathing and anti-apoptotic agent in cosmetic or topical dermatological preparations may rectify the disadvantages of the state of the art.

DETAILED DESCRIPTION

In separate pre-tests, idebenone was used in the macrophage LDL oxidation systems as anti-oxidant by way of comparison to alpha-tocopherol, ascorbic acid, coenzyme Q-10 and glutathione. This system is suitable for the simulation of cell-promoted oxidation of lipids induced by lipoxygenase, such as for example occurs due to UV radiation. To determine the antioxidative effect of the individual substances, the amount of primary degradation products of lipid peroxidation, the lipid hydroperoxides, occurring in the course of time after 8 or 24 hours was determined by means of an HPLC chemiluminescence method (E. Wieland et al., Fresenius J. Anal. Chem., 343, 62–63 (1992)). In spite of considerably lower concentration of idebenone in the batch (10 $\mu$moles/liter), a clearly stronger antioxidative effect was shown compared to ascorbic acid (50 $\mu$moles/liter), alpha-tocopherol (100 $\mu$moles/liter) and glutathione (50 $\mu$moles/liter). This was shown in particular when combining the remaining anti-oxidants with tocopherol. Only idebenone was able here to reliably intercept the pro-oxidative effect of tocopherol oxidation products occurring after 24 hours (see Table 1). Ascorbic acid in particular, which is occasionally added in cosmetic and topical dermatological preparations already containing tocopherol, showed in this combination in the course of time only a significantly lower antioxidative effect. The values given in the following tables relate to nmoles of measured lipid hydroperoxides per mg of LDL protein.

TABLE 1

Oxidation system (reference values)

| Time (hours) | Mk without additive | Mk + LDL (A) | A + 100 $\mu$moles/liter $\alpha$-tocopherol (B) | LDL without additive |
|---|---|---|---|---|
| 8 | 1.1 | 53.3 | 32.8 | 33.1 |
| 24 | 0 | 184.8 | 198.0 | 35.3 |

TABLE 2

Oxidation system (A) (+ 1 anti-oxidant)

| Time (hours) | A + 100 μmoles/litre α-tocopherol | A + 10 μmoles /litre idebenone | A + 50 μmoles/litre ascorbic acid | A + 50 μmoles/litre glutathione | A + 10 μmoles/ litre co-enzyme Q-1O |
|---|---|---|---|---|---|
| 8 | 32.8 | 0 | 0 | 51.7 | 69 |
| 24 | 198.0 | 0 | 1.7 | 119.0 | 115.8 |

TABLE 3

Oxidation system (B) (+ 1 further anti-oxidant)

| Time (hours) | B + 10 μmoles/litre idebenone | B + 50 μmoles/litre ascorbic acid | B + 50 μmoles/litre glutathione | B + 10 μmoles/litre coenzyme Q-10 |
|---|---|---|---|---|
| 8 | 1.9 | 1.7 | 23.3 | 26.8 |
| 24 | 2.6 | 25.3 | 129.8 | 143.7 |

Idebenone (6-(10-hydroxydecyl)-2,3-dimethoxy-5-methyl-1,4-benzoquinone) is characterised by the following structural formula:

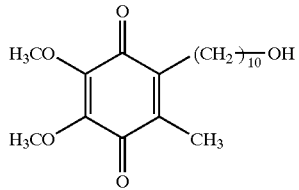

An example of a hydrophilic idebenone ester (separate synthesis):

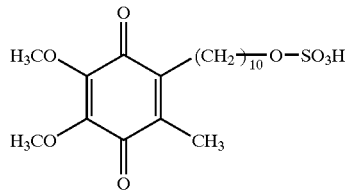

For the synthesis of idebenone ester (idebenone sulphonic acid), idebenone was reacted with pyridine-$SO_3$ and the reaction was then stopped using 1 N hydrochloric acid. After shaking out the organic phase using ethyl acetate, the organic phase was dried and concentrated under vacuum. The residue was dissolved in water and insoluble products centrifuged off. The hydrophilic idebenone ester thus recovered has excellent suitability for the application according to the invention in aqueous cosmetic and dermatological preparations.

However, there is no reference in these specifications which could point in the direction of the present invention.

It was therefore not possible for the expert to foresee that the idebenone used according to the invention and its derivatives or cosmetic or dermatological preparations containing them

- act better as anti-oxidant
- act better as free-radical absorbers/scavengers
- better prevent damage of lipids, DNA and proteins
- act better against skin aging and wrinkle formation
- better protect the skin against photo-reactions
- better prevent inflammatory reactions
- would better start regeneration processes in the skin than the active ingredients and preparations of the state of the art. Furthermore, it could not have been foreseen that idebenone and its derivatives in cosmetic or dermatological preparations have higher stability than comparable active ingredients, for example than vitamin C or vitamin E.

Pro-oxidative degradation products do not occur when using idebenone and/or its derivatives, or may be reliably intercepted when combining tocopherol and idebenone and/or its derivatives.

The use of idebenone and/or its derivatives, such as for example idebenone sulphonic acid is within the scope of the present invention. The use of other derivatives of idebenone is of course also within the scope of the present invention.

The use of idebenone and/or its derivatives as anti-oxidant and its use for combating and/or prophylaxis of skin aging caused by oxidative stress and inflammatory reactions are likewise within the scope of the present invention. The use of idebenone and/or its derivatives as anti-oxidants for the stabilisation of cosmetic or dermatological preparations, which contain as additive either vitamin A and/or its derivatives (for example all-E-retinoic acid, 9-Z-retinoic acid, 13-Z-retinoic acid, retinal, retinyl ester), vitamin B and/or its derivatives, vitamin C and/or its derivatives and vitamin E and/or its derivatives (for example alpha-tocopherol acetate) individually or in combination, is thus likewise within the scope of the present invention. The stabilising effect thus relates to both smell and colour and in particular to the active ingredient content of the preparation.

Furthermore, the use of idebenone and its derivatives as an agent for supporting vesicular breathing and stabilisation of mitochondrial membranes with additional anti-apoptotic effect in skin cells and its use for the regeneration and revitalisation of aging, stressed or damaged skin, is therefore within the scope of the present the invention.

The cosmetic or dermatological formulations of the invention may be composed as is conventional and serve for the treatment, care and cleansing of the skin and as a make-up product in decorative cosmetics. They preferably contain 0.0001 wt. % to 30 wt. %, preferably 0.05 wt. % to 5 wt. %, in particular 0.1–2.0 wt. %, based on the total weight of the agent, of idebenone and/or its derivatives.

For administration, the cosmetic and dermatological preparations of the invention are applied to the skin in adequate quantity in the manner conventional for cosmetics.

Cosmetic and dermatological preparations of the invention may exist in various forms. Hence, they may be, for example a solution, an anhydrous preparation, an emulsion or microemulsion of the type water-in-oil (W/O) or of the type oil-in-water (O/W), a multiple emulsion, for example of the type water-in-oil-in-water (W/O/W), a gel, a solid stick, an ointment or even an aerosol. It is also advantageous to administer idebenone and/or its derivatives in encapsulated form, for example in collagen matrices and other conventional encapsulation materials, for example as cellulose encapsulations, in gelatine, wax matrices or liposomally encapsulated.

It is also possible and advantageous within the scope of the present invention to add idebenone and/or its derivatives, here in particular the sulphate of idebenone, to aqueous systems or surfactant preparations for cleansing the skin.

The use of idebenone for the protection of the skin from oxidative stress is therefore also regarded as an advantageous embodiment of the present invention, in particular this use of idebenone in washing formulations.

The cosmetic and dermatological preparations of the invention may contain cosmetic auxiliaries, as are used conventionally in such preparations, for example preservatives, bactericides, perfumes, substances for preventing foaming, dyestuffs, pigments which have a colouring effect, thickening agents, surfactant substances, emulsifiers, softening, moisturising and/or moisture-retaining substances, fats, oils, waxes or other conventional constituents of a cosmetic or dermatological formulation, such as alcohols, polyols, polymers, foam stabilisers, electrolytes, organic solvents or silicone derivatives.

In particular, idebenone and its derivatives may also be combined according to the invention with other anti-oxidants and/or free-radical absorbers.

All anti-oxidants which are suitable or conventional for cosmetic and/or dermatological applications may be used according to the invention as favourable anti-oxidants.

The anti-oxidants are advantageously selected from the group consisting of amino acids (for example glycine, histidine, tyrosine, tryptophan) and their derivatives, imidazoles (for example urocanic acid) and their derivatives, peptides, such as D,L-camosine, D-carnosine, L-camosine and their derivatives (for example anserine), carotinoids, carotenes (for example alpha-carotene, beta-carotene, lycopene) and their derivatives, chlorogenic acid and its derivatives, lipoic acid and its derivatives (for example dihydrolipoic acid), aurothioglucose, propylthiouracil and other thiols (for example thioredoxin, glutathione, cysteine, cystine, cystamine and their glycosyl, N-acetyl, methyl, ethyl, propyl, amyl, butyl and lauryl, palmitoyl, oleyl, gamma-linoleyl, cholesteryl and glyceryl esters) and their salts, dilauryl thiodipropionate, distearyl thiodipropionate, thiodipropionic acid and their derivatives (esters, ethers, peptides, lipids, nucleotides, nucleosides and salts) and sulphoximine compounds (for example buthionine sulphoximines, homocysteine sulphoximine, buthionine sulphones, pentathionine sulphoximine, hexathionine sulphoximine, heptathionine sulphoximine) in very low, acceptable doses (for example pmole to µmoles/kg), also (metal) chelating agents (for example alpha-hydroxy fatty acids, palmitic acid, phytic acid, lactoferrin), alpha-hydroxy acids (for example citric acid, lactic acid, malic acid, mandelic acid), humic acid, colic acid, colic extracts, bilirubin, biliverdin, EDTA, EGTA and their derivatives, unsaturated fatty acids and their derivatives (for example gamma-linolenic acid, linolic acid, oleic acid), folic acid and their derivatives, ubiquinone and ubiquinol and their derivatives, vitamin C and derivatives (for example ascorbyl palmitate, Mg-ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and their derivatives, butylhydroxy toluene, butylhydroxy anisole, nordihydroguaiacic acid, nordihydroguaiaretic acid, trihydroxybutyrophenone, uric acid and its derivatives, mannose and its derivatives, sesamol, sesamolin, zinc and its derivatives (for example ZnO, $ZnSO_4$), selenium and its derivatives (for example selenium methionine), stilbenes and their derivatives (for example stilbene oxide, trans-stilbene oxide) and the suitable derivatives of the invention (salts, esters, ethers, sugars, nucleotides, nucleosides, peptides and lipids) of these said active ingredients.

The quantity of the aforementioned anti-oxidants (one or more compounds) in the preparations is preferably 0.0001 wt. % to 30 wt. %, particularly preferably 0.05 wt. % to 20 wt. %, in particular 1–10 wt. %, based on the total weight of the preparation.

Provided vitamin E and/or its derivatives represent the additional anti-oxidant(s), it is advantageous to select their particular concentration from the range from 0.0001–20 wt. %, based on the total weight of the formulation.

Provided vitamin A or vitamin A derivatives or carotenes or their derivatives represent the additional anti-oxidant(s), it is advantageous to select their particular concentrations from the range from 0.0001–10 wt. %, based on the total weight of the formulation.

Emulsions according to the present invention are advantageous and contain, for example the afore-mentioned fats, oils, waxes and other adipoids, and water and an emulsifier, as is used conventionally for such a type of formulation.

The lipid phase may advantageously be selected from the following substance group:

mineral oils, mineral waxes;

oils, such as triglycerides of capric or caprylic acid, also natural oils, such as for example castor oil;

fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids;

alkyl benzoates;

silicone oils, such as dimethylpolysiloxanes, diethylpolysiloxanes, diphenylpolysiloxanes and mixtures thereof.

The oil phase of the emulsions, oleogels or hydrodispersions or lipodispersions within the scope of the present invention is advantageously selected from the group of esters of saturated and/or unsaturated, branched and/or unbranched alkane carboxylic acids of chain length from 3 to 30 C atoms and saturated and/or unsaturated, branched and/or unbranched alcohols of chain length from 3 to 30 C atoms, from the group of esters from aromatic carboxylic acids and saturated and/or unsaturated, branched and/or unbranched alcohols of chain length from 3 to 30 C atoms. Such ester oils may then advantageously be selected from the group isopropyl myristate, isopropyl palmitate, isopropyl stearate, isopropyl oleate, n-butyl stearate, n-hexyl laurate, n-decyloleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic, and natural mixtures of such esters, for example jojoba oil.

Furthermore, the oil phase may advantageously be selected from the group of branched and unbranched hydrocarbons and waxes, silicone oils, dialkyl ethers, the group of saturated or unsaturated, branched or unbranched alcohols, and fatty acid triglycerides, namely the triglycerine esters of saturated and/or unsaturated, branched and/or unbranched alkane carboxylic acids of chain length from 8 to 24, in particular 12–18, C atoms. The fatty acid triglycerides may advantageously be selected, for example from the group of synthetic, semi-synthetic and natural oils, for example olive oil, sunflower oil, soybean oil, peanut oil, rape-seed oil, almond oil, palm oil, coconut oil, palm kernel oil and the like.

Also any mixtures of such oil and wax components can be used advantageously within the scope of the present invention. It may also optionally be advantageous to use waxes, for example cetyl palmitate, as the single lipid component of the oil phase.

The oil phase is advantageously selected from the group 2-ethylhexyl isostearate, octyl dodecanol, isotridecyl isononanoate, isoeicosane, 2-ethylhexyl cocoate, $C_{12-15}$ alkyl benzoate, capryl-capric acid triglyceride, dicaprylyl ether.

Mixtures of $C_{12-15}$ alkyl benzoate and 2-ethylhexyl isostearate, mixtures of $C_{12-15}$ alkyl benzoate and isotridecyl isononanoate and mixtures of $C_{12-15}$ alkyl benzoate, 2-ethylhexyl isostearate and isotridecyl isononanoate are particularly advantageous.

Of the hydrocarbons, paraffin oil, squalane and squalene can be used advantageously within the scope of the present invention.

The oil phase may advantageously also contain cyclic or linear silicone oils or may consist completely of such oils, but wherein it is preferable, apart from the silicone oil or the silicone oils, to use an additional amount of other oil phase components.

Cyclomethicone (octamethylcyclotetrasiloxane) is advantageously employed as silicone oil to be used according to the invention. However, other silicone oils should also advantageously be used within the scope of the present invention, for example hexamethylcyclotrisiloxane, polydimethylsiloxane, poly(methylphenylsiloxane).

Mixtures of cyclomethicone and isotridecyl isononanoate, of cyclomethicone and 2-ethylhexyl isostearate, are also particularly advantageous.

The aqueous phase of the preparations of the invention contains optionally advantageously alcohols, diols or polyols of low C number, and their ethers, preferably ethanol, isopropanol, propylene glycol, glycerine, ethylene glycol, ethylene glycol monoethyl or monobutyl ether, propylene glycol monomethyl, monoethyl or monobutyl ether, diethylene glycol monomethyl or monoethyl ether and analogous products, also alcohols of low C number, for example ethanol, isopropanol, 1,2-propane diol, glycerineand in particular one or more thickening agents, which may advantageously be selected from the group silicon dioxide, aluminium silicates, polysaccharides or their derivatives, for example hyaluronic acid, xanthan gum, hydroxypropylmethylcellulose, particularly advantageously from the group of polyacrylates, in each case individually or in combination.

Mixtures of the above-mentioned solvents are used in particular. For alcoholic solvents, water may be a further constituent.

Emulsions according to the present invention are advantageous and contain, for example the afore-mentioned fats, oils, waxes and other adipoids, and water and an emulsifier, as is used conventionally for such a type of formulation.

Gels according to the present invention conventionally contain alcohols of low C number, for example ethanol, isopropanol, 1,2-propane diol, glycerine and water or an above-mentioned oil in the presence of a thickening agent, which for oily-alcoholic gels is preferably silicon dioxide or an aluminium silicate, for aqueous-alcoholic or alcoholic gels is preferably a polyacrylate.

The conventional known highly volatile, liquefied propellants, for example hydrocarbons (propane, butane, isobutane), which may be used alone or mixed with one another, are suitable as propellants for preparations which can be sprayed from aerosol containers according to the present invention: Compressed air can also advantageously be used.

Preparations according to the present invention may also advantageously contain substances which absorb UV radiation in the UVB range, wherein the total quantity of filter substances is, for example 0.1 wt. % to 30 wt. %, preferably 0.5 to 10 wt. %, in particular 1.0 to 6.0 wt. %, based on the total weight of the preparations, in order to provide cosmetic preparations which protect the skin from the entire range of ultraviolet radiation. They may also serve as sunscreen agents for the skin.

If the preparations according to the present invention contain UVB filter substances, they may be oil-soluble or water-soluble. According to the invention, advantageous oil-soluble UVB filters are, for example:

mineral oils, mineral waxes;

oils, such as triglycerides of capric or caprylic acid, also natural oils, such as for example castor oil;

fats, waxes and other natural and synthetic adipoids, preferably esters of fatty acids with alcohols of low C number, for example with isopropanol, propylene glycol or glycerine, or esters of fatty alcohols with alkane acids of low C number or with fatty acids;

alkyl benzoates;

silicone oils, such as dimethylpolysiloxanes, diethylpolysiloxanes, diphenylpolysiloxanes and mixtures thereof.

3-benzylidene camphor derivatives, preferably 3-(4-methylbenzylidene) camphor, 3-benzylidene camphor;

4-aminobenzoic acid derivatives, preferably (2-ethylhexyl) 4-(dimethylamino) benzoate, amyl 4-(dimethylamino) benzoate;

esters of cinnamic acid, preferably (2-ethylhexyl) 4-methoxycinnamate, isopentyl 4-methoxycinnamate;

esters of salicylic acid, preferably (2-ethylhexyl) salicylate, (4-isopropyl-benzyl) salicylate, homomentyl salicylate, derivatives of benzophenone, preferably 2-hydroxy-4-methoxybenzophenone, 2-hy-droxy-4-methoxy-4'-methylbenzophenone, 2,2'-dihydroxy-4-methoxybenzophenone;

esters of benzylidenemalonic acid, preferably di(2-ethylhexyl) 4-methoxybenzylidenemalonate, -2,4,6-trianilino(p-carbo-2'-ethyl-1'hexyloxy)-1,3,5-triazine.

Advantageous water-soluble UVB filters are, for example:

salts of 2-phenylbenzimidazole-5-sulphonic acid, such as its sodium, potassium or its triethanol-ammonium salt, and the sulphonic acid itself;

sulphonic acid derivatives of benzophenones, preferably 2-hydroxy-4-methoxybenzophenone-5-sulphonic acid and their salts;

sulphonic acid derivatives of 3-benzylidene camphor, such as for example 4-(2-oxo-3-bornylidene-methyl) benzene sulphonic acid, 2-methyl-5-(2-oxo-3-bornylidene-methyl)sulphonic acid and their salts as well as 1,4-di(2-oxo-10-sulpho-3-bornylidene-methyl) benzene and its salts (the corresponding 10-sulphato compounds, for example the corresponding sodium, potassium or triethanol;-ammonium salt), also designated as benzene-1,4-di(2-oxo-1-bornylidene-methyl)-10-sulphonic acid.

The list of the said UVB filters, which may be used in combination with the active ingredient combinations of the present invention, should of course not be limiting.

Also within the scope of the present invention is the use of a combination of idebenone and/or its derivatives with at least one UVB filter as anti-oxidant or the use of a combination of idebenone and/or its derivatives with at least one UVB filter as anti-oxidant in a cosmetic or dermatological preparation.

It may also be advantageous to combine idebenone and/or its derivatives with UVA filters, which hitherto are conventionally present in cosmetic preparations. These substances are preferably derivatives of dibenzoylmethane, in particular 1-(4'-tert.butylphenyl)-3-(4'-methoxyphenyl)propane-1,3-dione and 1-phenyl-3-(4'-isopropyl-phenyl)propane-1,3-dione. These combinations or preparations which contain these combinations are also an object of the invention. The quantities used for the UVB combination may be used.

Also within the scope of the present invention is the use of a combination of idebenone and/or its derivatives with at least one UVA filter as anti-oxidant or the use of a combination of the active ingredient combinations of the invention with at least one UVA filter as anti-oxidant in a cosmetic or dermatological preparation.

Also within the scope of the present invention is the use of a combination of idebenone and/or its derivatives with at least one UVA filter and at least one UVB filter as anti-oxidant or the use of a combination of idebenone and/or its derivatives with at least one UVA filter and at least one UVB filter as anti-oxidant in a cosmetic or dermatological preparation.

Cosmetic and dermatological preparations having an effective amount of idebenone and/or its derivatives may also contain inorganic pigments, which are used conventionally in cosmetics to protect the skin from UV rays. They are oxides of titanium, zinc, zirconium, silicon, manganese, cerium and mixtures thereof, and modifications in which the oxides are the active agents. They are particularly preferably pigments based on titanium dioxide.

These combinations of UVA filters and pigment or preparations containing this combination are also within the scope of the present invention. The quantities mentioned for the above combinations may be used.

Cosmetic preparations which are a skin-cleansing agent or shampooing agent preferably contain at least one anionic, non-ionic or amphoteric surfactant substance, or also mixtures of such substances, idebenone and/or its derivatives in aqueous medium and auxiliaries, as are used conventionally therefor. The surfactant substance or the mixtures of these substances may be present in the shampooing agent in a concentration between 1 wt. % and 50 wt. %.

These cosmetic or dermatological preparations may also be aerosols having the auxiliaries conventionally used therefor.

Aqueous cosmetic cleansing agents of the invention or low-water or anhydrous cleansing agent concentrates intended for aqueous cleansing may contain anionic, non-ionic and/or amphoteric surfactants, for example traditional soaps, for example fatty acid salts of sodium alkyl sulphates, alkyl ether sulphates, alkane and alkyl benzene sulphonates sulphoacetates sulphobetaines sarcosinates amidosulphobetaines sulphosuccinates sulphosuccinic acid semi-esters alkyl ether carboxylates protein-fatty acid condensates alkylbetaines and amidobetaines fatty acid alkanol amides polyglycol ether derivatives.

Cosmetic preparations which are cosmetic cleansing preparations for the skin, may be present in liquid or solid form. In addition to idebenone and/or its derivatives, they preferably contain at least one anionic, non-ionic or amphoteric surfactant substance or mixtures thereof, if required one or more electrolytes and auxiliaries, as are used conventionally therefor. The surfactant substance may be present in the cleansing preparations in a concentration between 0.001 and 99.999 wt. %, based on the total weight of the preparations.

Cosmetic preparations which are a shampooing agent, in addition to a effective amount of idebenone and/or its derivatives, preferably contain an anionic, non-anionic or amphoteric surfactant substance or mixture thereof, optionally an electrolyte of the invention and auxiliaries, as are used conventionally therefor. The surfactant substance may be present in the shampooing agent in a concentration between 0.001 wt. % and 99.999 wt. %.

The compositions according to the present invention contain, apart from the afore-mentioned surfactants, water and optionally the additives which are conventional in cosmetics, for example perfume, thickener, dyestuffs, deodorants, antimicrobial materials, back-fatting agents, complexing and sequestering agents, pearlescent agents, plant extracts, vitamins and/ortheirderivatives, active ingredients and the like.

The present invention also includes a cosmetic process for protecting the skin and the hair from oxidative or photooxidative processes, which is characterised in that a cosmetic agent, which contains an effective concentration of idebenone and/or its derivatives, is applied to the skin or hair in adequate quantity.

Likewise, the present invention also includes a process for protecting cosmetic or dermatological preparations from oxidation or photooxidation, wherein these preparations, for example preparations for treating and caring for the hair are, in particular hair lacquers, shampooing agents, also make-up products, such as for example nail varnishes, lipsticks, foundations, washing and showering preparations, creams for treating or caring for skin or are all other cosmetic preparations, the constituents of which may bring with them stability problems due to oxidation or photooxidation on storage, characterised in that the cosmetic preparations have an effective amount of idebenone and/or its derivatives.

The quantity of idebenone and/or its derivatives in these preparations is preferably 0.0001–30 wt. %, preferably 0.05–5 wt. %, in particular 0.1–2.0 wt. %, based on the total weight of the preparations.

Also within the scope of the present invention are processes for producing the cosmetic agents of the invention, which is characterised in that active ingredient combinations of the invention are incorporated into cosmetic and dermatological formulations in a manner known per se.

The examples below are to illustrate the present invention without restricting it. All quantity details, proportions and percentage details are, unless otherwise stated, based on the weight and the total quantity or on the total weight of the preparations.

EXAMPLE 1

| O/W lotion | |
|---|---|
| | Wt. % |
| Paraffin oil (DAB 9) | 8.00 |
| Petrolatum | 4.00 |
| Octylmethoxy cinnamate | 5.00 |
| Isopropyl palmitate | 3.00 |
| Glycerine | 3.00 |
| Cetylstearyl alcohol | 2.00 |
| Butylmethoxy dibenzoylmethane | 1.00 |
| PEG-40 castor oil | 0.50 |
| Sodium cetylstearyl sulphate | 0.50 |
| Idebenone | 0.50 |
| Hyaluronate | 0.50 |
| Sodium carbomer | 0.40 |
| Alpha-tocopherol | 0.20 |
| Preservatives, dyestuffs, perfume | q.s. |
| Water | ad 100.00 |

EXAMPLE 2

| O/W cream | |
|---|---|
| | Wt. % |
| Paraffin oil 1 (DAB 9) | 7.00 |
| Avocado oil | 4.00 |
| Sodium lactate | 3.00 |
| Glycerine | 3.00 |
| Glyceryl monostearate | 2.00 |
| Titanium dioxide | 1.00 |
| Idebenone | 0.50 |
| Hyaluronate | 0.50 |
| Preservatives, dyestuffs, perfume | q.s. |
| Water | ad 100.00 |

EXAMPLE 3

| W/O cream | |
|---|---|
| | Wt. % |
| Paraffin oil (DAB 9) | 10.00 |
| Caprylic acid/capric acid triglyceride | 5.00 |
| Buxus Chinensis | 5.00 |
| Avocado Oil | 4.00 |
| PEG-40 hydrogenated castor oil | 4.00 |
| 1,2-Propylene glycol | 3.00 |
| Vaseline | 3.00 |
| Idebenone sulphonate | 1.00 |
| Alpha-tocopherol acetate | 1.00 |
| Retinol 10 CM | 1.00 |
| Paraben | 0.50 |
| Idebenone | 0.50 |
| Hyaluronate | 0.50 |

-continued

| W/O cream | |
|---|---|
| | Wt. % |
| Alpha-tocopherol | 0.50 |
| Preservatives, dyestuffs, perfume | q.s. |
| Water | ad 100.00 |

EXAMPLE 4

| Lip care stick | |
|---|---|
| | Wt. % |
| Petrolatum | 40.00 |
| Ceresin | 8.00 |
| Hydrogenated castor oil | 4.00 |
| Beeswax | 4.00 |
| Carnauba wax | 2.00 |
| Idebenone | 0.50 |
| β-Carotene | 0.10 |
| Preservatives, dyestuffs, perfume | q.s. |
| Paraffin oil | ad 100.00 |

EXAMPLE 5

| Lip care stick | |
|---|---|
| | Wt. % |
| Petrolatum | 40.00 |
| Isopropyl lanolate | 10.00 |
| Beeswax, bleached | 9.00 |
| Acetylated lanolin | 4.00 |
| Carnauba wax | 4.00 |
| Glycerine | 3.00 |
| Idebenone | 0.50 |
| Alpha-tocopherol acetate | 0.10 |
| Preservatives, dyestuffs, perfume | q.s. |
| Paraffin oil | ad 100.00 |

EXAMPLE 6

| Hair tonic | |
|---|---|
| | Wt. % |
| Ethanol | 40.00 |
| Idebenone | 0.50 |
| Alpha-tocopherol acetate | 0.50 |
| PEG-40 hydrogenated castor oil | 0.20 |
| Diisopropyl adipate | 0.10 |
| Preservatives, dyestuffs, perfume | q.s. |
| Water | ad 100.00 |

EXAMPLE 7

Liposome-containing gel

| | Wt. % |
|---|---|
| Lecithin | 6.00 |
| Sorbitol | 3.00 |
| Hydrolysed collagen | 2.00 |
| Xanthan gum | 1.40 |
| Sodium citrate | 0.50 |
| Sodium PCA | 0.50 |
| Idebenone | 0.50 |
| Glycine | 0.20 |
| Urea | 0.20 |
| Alpha-tocopherol | 0.20 |
| Biotin | 0.08 |
| Preservatives, dyestuffs, perfume | q.s. |
| Water | ad 100.00 |

EXAMPLE 8

Sunscreen emulsion

| | Wt. % |
|---|---|
| Octylmethoxy cinnamate | 5.00 |
| Castor oil | 4.00 |
| Glycerine | 3.00 |
| Octyl stearate | 3.00 |
| Laurylmethicone copolyol | 2.00 |
| Cyclomethicone | 2.00 |
| Cetylstearyl alcohol | 1.80 |
| Na$_3$HEDTA | 1.50 |
| Glycerol lanolate | 1.00 |
| Butylmethoxy dibenzoylmethane | 1.00 |
| Idebenone | 0.50 |
| PEG-40 hydrogenated castor oil | 0.30 |
| Sodium cetylstearyl sulphate | 0.30 |
| Acrylamide/sodium acrylate copolymer | 0.30 |
| Alpha-tocopherol | 0.20 |
| Caprylic acid/capric acid triglyceride | 0.10 |
| Preservatives, dyestuffs, perfume | q.s. |
| Water | ad 100.00 |

EXAMPLE 9

Sunscreen emulsion

| | Wt. % |
|---|---|
| Caprylic acid/capric acid triglyceride | 6.00 |
| Octylmethoxy cinnamate | 5.00 |
| Butylmethoxy dibenzoylmethane | 4.00 |
| PEG 22-dodecyl copolymer | 3.00 |
| Paraffin oil (DAB9) | 2.00 |
| Cyclomethicone | 2.00 |
| Idebenone | 0.50 |
| Alpha-tocopherol acetate | 0.50 |
| Na$_3$HEDTA | 0.50 |
| Cetyldimethicone copolyol | 0.20 |
| Preservatives, dyestuffs, perfume | q.s. |
| Water | ad 100.00 |

EXAMPLE 10

Sunscreen emulsion

| | Wt. % |
|---|---|
| Octylmethoxy cinnamate | 4.00 |
| Castor oil | 4.00 |
| Octyl stearate | 3.00 |
| Glycerine | 3.00 |
| Cyclomethicone | 2.00 |
| Laurylmethicone copolyol | 2.00 |
| Cetylstearyl alcohol | 1.70 |
| Na$_3$HEDTA | 1.50 |
| Glycerol lanolate | 1.00 |
| Butylmethoxy dibenzoylmethane | 1.00 |
| Alpha-tocopherol acetate | 1.00 |
| Idebenone | 0.50 |
| PEG-40 hydrogenated castor oil | 0.40 |
| Sodium cetylstearyl sulphate | 0.30 |
| Acrylamide/sodium acrylate copolymer | 0.30 |
| Hydroxypropylmethylcellulose | 0.30 |
| Caprylic acid/capric acid triglyceride | 0.10 |
| Preservatives, dyestuffs, perfume | q.s. |
| Water | ad 100.00 |

EXAMPLE 11

Gel

| | Wt. % |
|---|---|
| Triethanolamine | 3.00 |
| Carbopol 934 P | 2.00 |
| Hydrolysed collagen | 2.00 |
| Glycerine | 2.00 |
| Sodium PCA | 0.50 |
| Idebenone | 0.50 |
| Alpha-tocopherol acetate | 0.20 |
| Preservatives, dyestuffs, perfume | q.s. |
| Water | ad 100.00 |

EXAMPLE 12

Spray formulation

| | Wt. % |
|---|---|
| Ethanol | 30.00 |
| Idebenone | 0.50 |
| Alpha-tocopherol acetate | 0.10 |
| Preservatives, dyestuffs, perfume | q.s. |
| Propane/butane 25/75 | ad 100.00 |

What is claimed is:

1. A method for treating a skin change comprising applying a topical preparation to the skin, the preparation comprising an amount of an agent effective for treating the skin change, the agent comprising idebenone, a derivative of idebenone, or a combination of idebenone and the derivative of idebenone.

2. The method as recited in claim 1 wherein the skin change includes an aging of the skin.

3. The method as recited in claim 1 wherein the skin change includes a wrinkling of the skin.

4. The method as recited in claim 1 wherein the skin change includes a damage of the skin by ultraviolet light.

5. The method as recited in claim 1 wherein the skin change includes an oxidative process.

6. The method as recited in claim 1 wherein the skin change includes a degenerative process.

7. The method as recited in claim 1 wherein the agent acts as an antioxidant.

8. The method as recited in claim 1 wherein the agent acts as a radical scavenger.

9. The method as recited in claim 1 wherein the agent acts as a stabilizer of skin cells.

10. The method as recited in claim 1 wherein the agent acts as a stabilizer of mitocondria membranes of skin cells.

11. The method as recited in claim 1 wherein the agent supports cellular respiration of skin cells so as to promote regeneration of the cells.

12. The method as recited in claim 1 wherein the agent protects the skin upon damage to the skin using an anti-apoptotic property of the respective idebenone, a derivative of idebenone, or a combination of idebenone and a derivative of idebenone.

13. The method as recited in claim 1 wherein the derivative of idebenone is a hydrophilic ester of idebenone.

14. The method as recited in claim 1 wherein the derivative of idebenone is a sulfonic acid ester of idebenone.

15. The method as recited in claim 1 wherein the derivative of idebenone is at least one of an ester of idebenone and an ester of the derivative of idebenone.

16. The method as recited in claim 1 wherein the topical preparation further comprises at least one of a glycosaminoglycan, a derivative of a glycosaminoglycan and a hyaluronidase inhibitor.

17. The method as recited in claim 1 wherein the topical preparation further comprises a cosmetic auxiliary.

18. The method as recited in claim 1 wherein the agent stabilizes another component of the preparation.

19. The method as recited in claim 18 wherein the other component includes at least one of vitamin A, a derivative of vitamin A, vitamin B, a derivative of vitamin B, vitamin C, a derivative of vitamin C, vitamin E, a derivative of vitamin C, hyaluronic acid and a derivative of hyaluronic acid.

20. The method as recited in claim 19 wherein the at least one of hyaluronic acid and a derivative of hyaluronic acid has a molecular weight of up to 1,000,000.

21. The method as recited in claim 1 wherein the topical preparation further comprises another antioxidant.

22. The method as recited in claim 1 wherein the agent protects another component of the preparation from an oxidation process.

23. The method as recited in claim 1 wherein the preparation further comprises at least one ultraviolet filter.

24. The method as recited in claim 1 wherein the preparation includes an emulsion.

25. The method as recited in claim 1 wherein the preparation includes a gel.

26. The method as recited in claim 1 wherein the idebenone, a derivative of idebenone, or a combination of idebenone and a derivative of idebenone has a concentration of from about 0.0001 to about 30% by weight of the preparation.

27. The method as recited in claim 1 wherein idebenone, a derivative of idebenone, or a combination of idebenone and a derivative of idebenone has a concentration of from about 0.05 to about 5% by weight of the preparation.

28. The method as recited in claim 1 wherein the idebenone, a derivative of idebenone, or a combination of idebenone and a derivative of idebenone has a concentration of from about 0.1 to about 2.0% by weight of the preparation.

29. The method as recited in claim 1 wherein the preparation is a cosmetic preparation.

30. The method as recited in claim 1 wherein the preparation is a dermatological preparation.

31. A method for treating a skin change comprising:

providing a person in need of treatment of the skin change, the skin change being responsive to an application of idebenone, a derivative of idebenone, or a combination of idebenone and the derivative of idebenone; and applying an amount of the idebenone, the derivative of idebenone, or the combination of idebenone and the derivative of idebenone, effective for treating the skin change.

32. The method as recited in claim 31 wherein the skin change includes an aging of the skin.

33. The method as recited in claim 31 wherein the skin change includes a wrinkling of the skin.

34. The method as recited in claim 31 wherein the skin change includes an oxidative process.

35. The method as recited in claim 31 wherein the skin change includes a degenerative process.

36. The method as recited in claim 31 wherein the applying is included in a cleansing of the skin.

37. The method as recited in claim 31 wherein the applying is included in a cosmetic treatment of the skin.

38. A method for protecting a component of a topical skin preparation from an oxidation process, the method comprising including an amount of idebenone, a derivative of idebenone, or a combination of idebenone and the derivative of idebenone effective to protect the component from the oxidation process.

39. The method as recited in claim 13 wherein the topical skin preparation further comprises at least one compound selected from the group consisting of an alpha-hydroxy acid, vitamin A and a vitamin A derivative.

40. The method as recited in claim 39 wherein the alpha-hydroxy acid is at least one of citric acid, lactic acid, malic acid and mandelic acid.

41. The method as recited in claim 39 wherein the at least one compound has a concentration of from about 0.0001 to about 30% by weight of the preparation.

42. The method as recited in claim 41 wherein the at least one compound has a concentration of from about 0.05 to about 20% by weight of the preparation.

43. The method as recited in claim 42 wherein the at least one compound has a concentration of about 1 to about 10% by weight of the preparation.

44. The method as recited in claim 39 wherein the at least one compound is selected from the group consisting of vitamin A and a vitamin A derivative, the at least one compound having a concentration of from about 0.0001 to about 10% by weight of the preparation.

* * * * *